United States Patent [19]

Smith et al.

[11] Patent Number: 5,024,670

[45] Date of Patent: Jun. 18, 1991

[54] POLYMERIC BEARING COMPONENT

[75] Inventors: Todd S. Smith, Warsaw; David C. Kelman, Winona Lake, both of Ind.

[73] Assignee: DePuy, Division of Boehringer Mannheim Corporation, Indianapolis, Ind.

[21] Appl. No.: 416,139

[22] Filed: Oct. 2, 1989

[51] Int. Cl.$^5$ ............................ A61F 2/30; A61F 2/38
[52] U.S. Cl. .......................................... 623/18; 623/20
[58] Field of Search ........................ 623/18, 20, 22, 23

[56] References Cited

U.S. PATENT DOCUMENTS

| | | |
|---|---|---|
| 3,022,814 | 2/1962 | Bodine, Jr. . |
| 3,184,353 | 5/1965 | Balamuth et al. . |
| 4,106,962 | 8/1978 | Adams et al. . |
| 4,356,926 | 11/1982 | Priestly et al. . |
| 4,358,328 | 11/1982 | Pearson . |
| 4,550,448 | 11/1985 | Kenna ................................... 623/16 |
| 4,556,138 | 1/1986 | Lewis et al. . |
| 4,644,942 | 2/1987 | Sump . |
| 4,778,469 | 10/1988 | Lin et al. . |
| 4,813,960 | 3/1989 | Muller .................................. 623/22 |

FOREIGN PATENT DOCUMENTS 3331-562 9/1983 Fed. Rep. of Germany .

*Primary Examiner*—Alan W. Cannon
*Attorney, Agent, or Firm*—Barnes & Thornburg

[57] ABSTRACT

A method of joining a polymeric part and a metallic or ceramic part. The result is a bearing for an orthopedic prosthesis comprising a rigid backing component presenting a mating surface having interstices, a polymeric bearing component having a corresponding mating surface, the bearing component and backing components being joined together by heating the backing component to a temperature sufficient to reduce the viscosity of the bearing component at its mating surface and by forcing the components together with sufficient pressure to cause the bearing component mating surface to flow into the interstices of the backing component mating surface.

11 Claims, 1 Drawing Sheet

POLYMERIC BEARING COMPONENT

FIELD OF THE INVENTION

The present invention relates generally to a method of joining a polymeric part and a metallic or ceramic part which must function as one component in an orthopedic implant device.

DESCRIPTION OF THE PRIOR ART

The articulation of metallic components against metallic components in an implant device results in high wear rates and generation of unacceptable amounts of wear debris. Thus, a substitution of a polymeric component for one of the metallic components dramatically reduces the rate of wear of the components. Due to the differences in mechanical properties of the substituted polymeric material as compared to the metallic component, some components should not be completely fabricated from an all polymeric component. In other situations, an all polymeric material component might have sufficient mechanical strength but does not distribute the stresses to the bone as evenly as a metallic component. A hybrid system has evolved in which the articulation surface is of polymeric material for improved wear performance, and the backing produced from either a metallic or ceramic material, for more uniform stress transfer and for biological ingrowth. It will be understood that a ceramic material could be substituted for the metallic material and that all further reference to a metallic material is intended to refer also to ceramic material.

In the past, to attach the polymeric part to the metallic part, the polymeric part and the metallic component are machined in such a way that an interference fit exists between the two. Generally the location of the interference fit may be around the circumference of the parts or a male-female structure may be placed at the interface between the two parts. The two parts may be assembled by simply applying sufficient force to snap the parts together. In such an arrangement, the locking engagement prevents disassembly of the parts. A variation of this method is to utilize the difference in the thermal coefficients of expansion of the polymeric and the metallic parts. The temperature of one part (male) is substantially lowered, which reduces the dimensions of the part sufficiently that it can be mated with the other component (female). The part that has been reduced in temperature returns to ambient temperature during which the part expands and is in forced contact with the mating part. The two parts are held in place by an interference contact. The mechanical interference fit method requires precise manufacturing of both the polymeric and metallic parts. Exact machining of the polymeric part is difficult to perform as the material will elastically deform during the act of machining, thereby yielding widely varying dimensions.

Another alternative attachment method is to mold the polymeric material around the metallic part. The metallic part is designed such that, during the molding operation, the polymeric material flows around or into protrusions or intrusions intended to secure the polymer to the metallic component. The molding process can be very time consuming and is extremely sensitive to process parameters of temperature, pressure and time.

U.S. Pat. No. 4,566,138 to Lewis, et al. discloses another prior art technique for securing a polymer, polymethylmethacrylate (PMMA), to a metallic prosthesis. This technique for adhering spacers to a porous surface utilizes a sonic welding method. The contacting of the acrylic spacer surface to the porous surface melts and flows into the porous surfaces and then hardens upon the removal of the ultrasound energy. Such acrylic materials have good melt-flow characteristics. The concept of sonic welding as described by Lewis et al, is only feasible for materials which will melt and have good melt-flow characteristics.

The present invention provides a means of securing a polymeric bearing compound to a more rigid backing component. Briefly stated, a polymeric bearing component produced by molding or machining is forced onto a hot porous coated metallic or ceramic backing component. The heat in the hot component supplies the thermal energy necessary to sufficiently reduce the viscosity of the immediate adjacent polymer zone such that it becomes impregnated into a textured or porous layer of the backing component with the application of pressure. A machined or laser produced surface of sufficient roughness and undercuts would possibly also work with this method. The interdigitated polymer within the porous coating of the rigid backing component results in a mechanical bond of tremendous strength, thus holding the bearing component secure to the rigid backing component. The reduction of the viscosity of the polymeric component substantially reduces the resistance of the material to creep. With the application of sufficient pressure, the polymeric material creeps into the cavities and interstices of the backing component. Upon returning to ambient temperature, the viscosity of the material in the adjacent zone will revert back to the original value. At the original viscosity level, the resistance to creep will also return to or very near the original resistance level. The mechanical strength of the polymer component at ambient temperature becomes such that it is well fixed to the backing component.

The polymeric component may typically be of an ethylene group, i.e., Ultra-High-Molecular-Weight Polyethylene (UHMWPe), but should work with any polymer where the viscosity can be reduced sufficiently with the application of thermal energy such that it will creep into and around texture surface irregularities of the backing component. By decreasing the viscosity of the polymer the mechanical properties of the material are also reduced, in particular the creep and tensile properties. With the reduced mechanical properties the material is less resistant to deformation due to applied stress, i.e., pressure. With the application of pressure the polymeric material is force to deform into the irregularities and/or porosity of the rigid backing component. Upon achieving ambient temperature the mechanical properties return to the original high levels and provide a strong mechanical bond between the two components. Polymeric material that would be applicable to this invention typically would not melt-flow or liquefy at or near its melt point. These polymeric materials do not have a true melting point. If the temperature becomes too great the polymeric material begins to deteriorate and upon cooling to ambient temperature will have inadequate mechanical properties.

The backing component is constructed such that a surface is textured sufficiently such that the polymeric material can be forced into the irregularities or porosity of the backing surface and anchor itself by interdigitating with the surface irregularities. The backing component can have a textured surface, completely porous structure through its cross section or it can have a surface layer of porosity. The surface layer of porosity can be similar to that described in U.S. Pat. No. 3,605,123 to Hahn or U.S. Pat. No. 3,855,638 to Pilliar. In this description and in the claims, the word "porous" is intended broadly to specify a surface which provides interstices into which polymeric material may flow no matter how the interstices are provided.

It is an object of the present invention, therefore, to provide a bearing for an orthopedic prosthesis comprising a rigid backing component presenting a mating surface having interstices, a polymeric bearing component having a corresponding mating surface, the bearing component and backing components being joined together by heating the backing component to a temperature sufficient to reduce the viscosity of the bearing component at its mating surface and by forcing the components together with sufficient pressure to cause the bearing component mating surface to flow into the interstices of the backing component mating surface.

It is another object of the present invention to provide such a bearing in which the rigid backing component is made of titanium and its mating surface is provided by sintering particles of titanium to the backing component while the bearing component is made of UHMWPe. The backing component is heated to a temperature between 1.4 and 2.2 times the Crystalline Melt Point of UHMWPe. The components are forced together under pressures and for periods of times sufficient to cause the flowing of the polymeric material into the porous metal coating.

Other objects and features of the present invention will become apparent as this description progresses.

DETAILED DESCRIPTION OF THE INVENTION

The present invention will be described with reference to a patella prosthesis, although it is understood that the principles of this invention may be applied to other prosthetic components.

Figure 1:
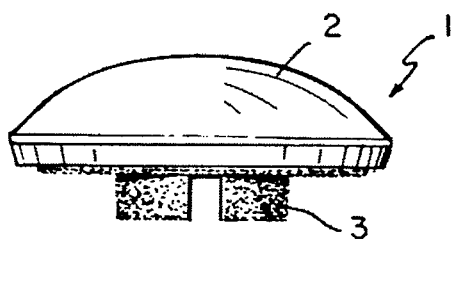
FIG. 1 is a perspective view of a prosthetic patella button made in accordance with the present invention.
Figure 2:
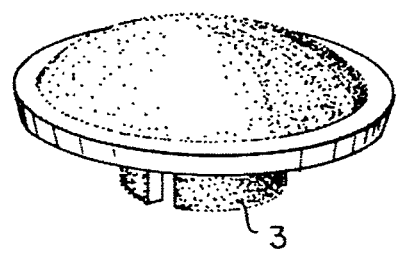
FIG. 2 is a perspective view of the backing component of the patella button showing the porous surface which is forced into the polymeric bearing components.

Referring to FIGS. 1 and 2 which illustrate a particular embodiment of a patella button prosthesis according to the present invention, the patella button 1 comprises an outer bearing surface component 2 and a backing component 3.

The outer bearing component 2 may be of a multitude of geometries. The geometries may be symmetrical or non-symmetrical in relation to the center of the component. The material is typically of a polymeric type, with substantially superior articulation properties than that of the backing component 3 metallic material.

The backing component 3 material typically is a more rigid material having greater modulus of elasticity than the bearing component for improved stress transfer to the adjacent bone. The backing component 3 would preferably either be textured have a porous layer, or be completely porous to provide sites to anchor the polymeric bearing component 2. The temperature of the rigid backing component 3 is elevated to a level at which sufficient thermal energy can be transferred to the polymeric component 2 to locally reduce the viscosity. The lowering of the viscosity of the polymeric material reduces the mechanical properties of the material, particularly creep and tensile strength, such that with the application of sufficient force the polymeric material interdigitates with the textured or porous coating. Only a narrow zone of polymeric material parallel to the surface of the rigid backing component 3 making contact with the backing component is lowered in viscosity. The low thermal conductivity of the polymeric material and the limited amount of thermal energy imparted to the backing component 3 restricts the amount of material for which the viscosity will be lowered. The outside surface material of the bearing component which articulates against a mating orthopedic device is totally unaffected by the bonding process, as very little thermal energy is transmitted to that surface. Thermal energy input should preferably be carefully controlled because if the polymeric component is exposed to excessive temperatures, the molecular chain will be broken down reducing the molecular weight of the material. In the case of Ultra-High-Molecular-Weight Polyethylene (UHMWPe), as the molecular weight decreases the resistance to wear also decreases.

The following examples are provided better to describe the invention.

EXAMPLE 1

A titanium porous coated rigid backing component 3 was elevated to a temperature of 1.4 times the Crystalline Melt Point of Ultra-High-Molecular-Weight Polyethylene (UHMWPe). The Crystalline Melt Point of a Polymer is defined as "first order transition in crystalline polymers. The fixed point between the solid and liquid phases of a material when approached from the solid phase under a pressure of 1 atmosphere". Once thermal equilibrium was achieved the component was mated to the correspondingly machined UHMWPe bearing component. A pressure of 1150 psi was applied between components to interdigitate the polymeric material into the porous coating. The assembly was maintained under pressure for 120 seconds.

EXAMPLE 2

A titanium porous coated rigid backing component 3 was elevated to 1.7 times the Crystalline Melt Point of UHMWPe. The rigid backing component and UHMWPe bearing component were assembled with a pressure of 1150 psi applied for 120 seconds.

EXAMPLE 3

The titanium porous coated backing component 3 was elevated to 2.2 times the Crystalline Melt Point of UHMWPe. An assembly pressure of 1350 psi for 120 seconds was applied to the UHMWPe bearing and backing component.

Favorable results were obtained with all three sets of parameters, but the parameters of Example 2 seem more preferred.

Figure 3:
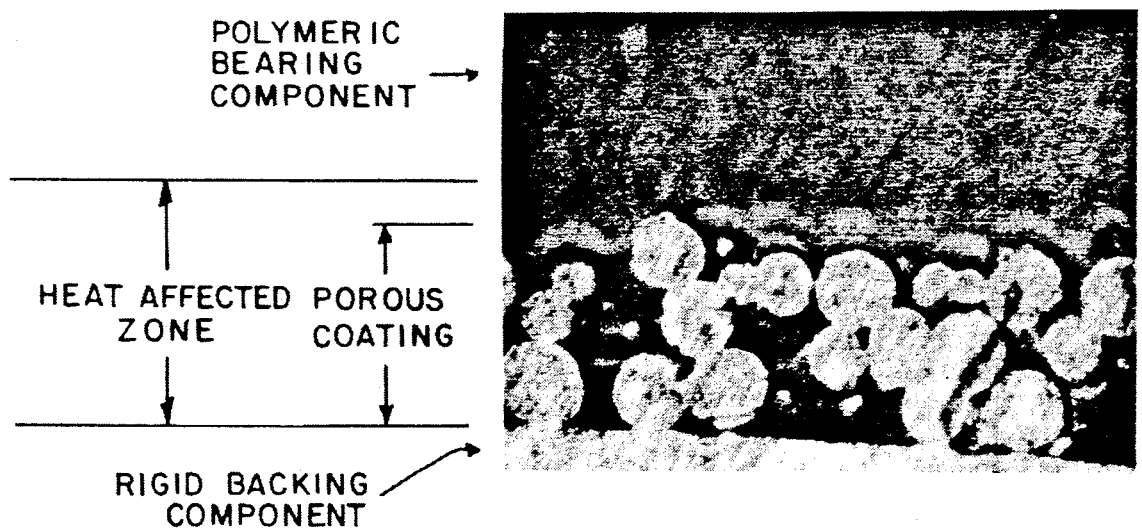
FIG. 3 is a fragmentary perspective view of a section of the patella button showing how the polymeric material flows into the porous surface in accordance with the present invention.

It will be appreciated that the use of porous metal coatings on metallic orthopedic implant devices is well known throughout the orthopedic trade. Typically, a rigid component is made from a metal such as titanium and small titanium beads of various sizes and depths are sintered to the component to provide a porous surface. Typically, this porous surface is provided to accommodate what is referred to as "bone ingrowth," i.e., the growth of bone tissue into the implant device to secure and stabilize the device. It has been found that such porous surfaces intended for bone ingrowth are very satisfactory for the mechanical connection of the present invention. Typically, sintered titanium beads having a size of 177-250 microns will be sintered to the titanium base metal to a depth of 0.75 millimeters. This sintering process will provide interstices similar to that shown in FIG. 3. The polymeric bearing material flows into these interstiCes as described above to provide a secure connection between the bearing component and the backing component.

What is claimed is:

1. A load bearing support for an orthopedic prosthesis component comprising a rigid backing component presenting a rigid mating surface having interstices, a polymeric bearing component having a load supporting surface allowing for repeated movable contact with another prosthesis component and wherein said polymeric bearing component also has a corresponding mating surface, said bearing component and backing component being joined together by heating said backing component to a temperature sufficient to reduce the viscosity of the bearing component at its mating surface and by forcing said components together continuously along the mating surfaces with sufficient pressure to cause the bearing component mating surface to flow into the interstices of the backing component mating surface.

2. The bearing of claim 1 in which said bearing component is made of UHMWPe and said backing component is made of metal suitable for orthopedic implants having at least its mating surface coated with particles of said metal to provide a porous coating having interstices into which said polymeric material may flow under heat and pressure.

3. The bearing of claim 2 in which said metal is titanium and said particles are sintered at least to said backing component mating surface.

4. The bearing of claim 3 in which said backing component is heated to about 1.7 times the Crystalline Melt Point of UHMWPe and said components are pressed together with a pressure of about 1150 psi for about 120 seconds.

5. The bearing of claim 3 in which said backing component is heated to a temperature between about 1.4 and 2.2 times the Crystalline Melt Point of UHMWPe and said components are forces together with sufficient pressure for sufficient time to cause said polymeric material to flow into said metal porous coating such that, when said components are cooled, there is a strong mechanical bond therebetween.

6. A load bearing support for an orthopedic prosthesis component comprising a rigid metal backing component having a porous metallic rigid mating surface providing interstices, and a polymeric bearing component having a load supporting surface allowing for repeated movable contact with another prosthesis component and wherein said polymeric bearing component also has a mating surface in continuous mechanical engagement with said backing component along its mating surface, said mechanical engagement being provided by portions of said bearing components which have flowed into said interstices under the application of heat and pressure.

7. The bearing of claim 6 in which said mechanical engagement is accomplished by heating said metal backing component to a temperature sufficient to reduce the viscosity of the mating surface of said bearing component and by applying sufficient pressure between said components for a sufficient period of time mechanically to join said components.

8. A method for joining a rigid backing component and a polymeric load bearing component of an orthopedic device having a load supporting surface allowing for repeated movable contact with another prosthesis component and wherein said polymeric bearing component also has a bearing mating surface comprising the steps of providing a porous coating continuous with and on a rigid mating surface of said backing component, heating said backing component to a temperature sufficient to reduce the viscosity of at least the corresponding bearing mating surface on said polymeric bearing, forcing said components together with sufficient pressure for sufficient time to cause said bearing mating surface of said polymeric load bearing component to continuously cover and flow into said porous coating while retaining the load support surface of the polymeric load bearing component.

9. The method of claim 8 in which said backing component is titanium and said porous coating is formed by particles of titanium sintered to said backing component and said polymeric bearing is made of UHMWPe, said backing component being heated to a temperature between about 1.4 to 2.2 times the Crystalline Melt Point of UHMWPe.

10. The method of claim 9 in which said forcing step is carried out at pressures between about 1150 and 1350 psi.

11. The method of claim 10 in which said forcing step is applied for about 120 seconds.

* * * * *